United States Patent
Yamamoto et al.

[11] Patent Number: 6,030,839
[45] Date of Patent: Feb. 29, 2000

[54] METHOD FOR DETERMINING SODIUM CONCENTRATION IN ALCOHOL

[75] Inventors: Shinpei Yamamoto, Ibaraki-ken; Satoru Nakai, Mito; Toshio Yatabe, Ibaraki-ken, all of Japan

[73] Assignee: Japan Nuclear Cycle Development Institute, Japan

[21] Appl. No.: 09/036,686

[22] Filed: Mar. 9, 1998

[30] Foreign Application Priority Data

Aug. 27, 1997 [JP] Japan ..................................... 9-231015

[51] Int. Cl.⁷ .................................................. G01N 33/20
[52] U.S. Cl. .................. 436/79; 73/149; 73/150
[58] Field of Search ................................ 436/73, 79, 149, 436/150

[56] References Cited

FOREIGN PATENT DOCUMENTS

| 53-89491 | 8/1978 | Japan . |
| 56-39440 | 9/1981 | Japan . |
| 57-146200 | 9/1982 | Japan . |

OTHER PUBLICATIONS

L. E. Chulos BNWL–637, 1967, Report.
J. Barthel et al. *Z. Phys. Chem.* 1970, 72, 50–58.
J. De Jonge *Hung, J. Ind. Chem.* 1975, 3, 497–518.
F. H. Welch et al. Report, 1977, AI–ERDA–13/92.
R. Caponetti *Nuclear Technol.* 1985, 70, 408–423.
1997 (35th) Annual Meeting of the Atomic Energy Society of Japan, Preliminary Report (Mar. 1997).

*Primary Examiner*—Arlen Soderquist
*Attorney, Agent, or Firm*—Wenderoth, Lind & Ponack, L.L.P.

[57] ABSTRACT

Preparations are made of a characteristic curve of conductivity showing the relationship between sodium concentration in alcohol and conductivity of alcohol as observed at a predetermined temperature and a temperature correction curve showing the change in conductivity per unit degree centigrade of alcohol temperature versus; sodium concentration in alcohol; the corrected conductivity of a sample alcohol is determined by measuring the conductivity and temperature of the sample alcohol simultaneously and subjecting the measured conductivity to temperature correction according to the above temperature correction curve; and then the sodium concentration in the sample alcohol is determined on the basis of the corrected conductivity thus obtained. Thus, the change in sodium concentration in alcohol can be measured and monitored continuously and accurately.

1 Claim, 1 Drawing Sheet

METHOD FOR DETERMINING SODIUM CONCENTRATION IN ALCOHOL

BACKGROUND OF THE INVENTION

The present invention relates to a method for determining sodium concentration in alcohol, which is effectively usable for speedy and accurate determination of sodium concentration in an alcoholic washing fluid used in the removal of sodium adherent to the sodium-related equipments or the like of a fast breeder reactor using liquid sodium as a coolant.

Sodium removal by alcohol is widely employed in Japan and abroad, because it is considered that the reactions occurring in this removal are so mild that the structural material of sodium-related equipments is little affected by the removal.

In the above sodium removal, determination of sodium concentration in alcohol is necessary for grasping the progress of the removal or judging the completion of the removal. Up to this time, the quantity of sodium dissolved in alcohol has been determined by neutralization titration. According to this method, however, it took about one hour to conduct one analyzing run, so that the sampling had to be conducted at intervals of 1 to 2 hours. Accordingly, it was impossible to determine or monitor the progress of the removal continuously by this method. The neutralization titration therefore had the problem that the timing of discontinuing the removal or a suitable timing of exchanging the alcoholic washing fluid could not be determined exactly.

Although the determination of sodium concentration in alcohol has been conducted also by measuring the conductivity of alcohol, the characteristics, quantitativeness or applicability of this method has not been elucidated at all, so that it was difficult to accurately determine sodium concentration in alcohol on the basis of the conductivity of alcohol. Accordingly, the determination of sodium concentration in alcohol on the basis of the conductivity has been employed merely as auxiliary means for determining the progress of sodium removal.

SUMMARY OF THE INVENTION

An object of the present invention is to solve the above-described problems of the prior art methods and to provide a method for determining sodium concentration in alcohol, by which the change in sodium concentration in alcohol can be determined and monitored continuously and accurately, so that the completion of the removal or the timing of exchanging the alcoholic washing fluid can be judged speedily and exactly.

The inventors of the present invention have found that the conductivity of alcohol depends not only on the sodium concentration in alcohol but also on the alcohol temperature significantly and that the determination of a correct sodium concentration in alcohol cannot therefore be attained merely by measuring the conductivity of alcohol, but includes measuring the conductivity and temperature of alcohol simultaneously and subjecting the measured conductivity to temperature correction. The present invention has been accomplished on the basis of these findings.

Namely, the method for determining sodium concentration in alcohol according to the present invention comprises preparing a characteristic curve of conductivity showing the relationship between sodium concentration in alcohol and conductivity of alcohol as observed at a predetermined temperature and a temperature correction curve showing the change in conductivity per unit degree centigrade (° C.) of alcohol temperature versus sodium concentration in alcohol, measuring the conductivity and temperature of a sample alcohol simultaneously, subjecting the measured conductivity to temperature correction according to the temperature correction curve, and determining the sodium concentration in the sample alcohol on the basis of the corrected conductivity thus obtained.

DESCRIPTION OF THE PREFERRED EMBODIMENTS

Sodium removal by alcohol will now be described as an embodiment for carrying out the present invention.

In general, the removal of sodium is carried out by using an alcohol containing ethyl alcohol as the main component, though propyl alcohol and other alcohols can also be used therefor.

The sodium-removing power of an alcoholic washing fluid used in the removal is remarkably poor, when the fluid contains sodium in an amount exceeding 5 wt %. In the removal of sodium by alcohol, therefore, the sodium concentration of the alcoholic washing fluid is required to be 5 wt % or below. In other words, although an alcoholic washing fluid can be circulated and re-used as far as the sodium concentration of the fluid is lower than 5 wt %, the fluid must be exchanged immediately when the sodium concentration of the fluid has reached 5 wt %.

Meanwhile, the alcohol temperature in the sodium removal must be 0 to 50° C. Although alcohol is poor in sodium-removing power at a temperature lower than 0° C., in general, the temperature of the washing fluid used in the removal of sodium does not become lower than 0° C. On the other hand, an alcohol temperature exceeding 50° C. brings about a danger of combustion or explosion. Accordingly, it is preferable from the standpoint of securing safeness that the alcohol temperature in sodium removal be lower than 50° C.

Figure 1:
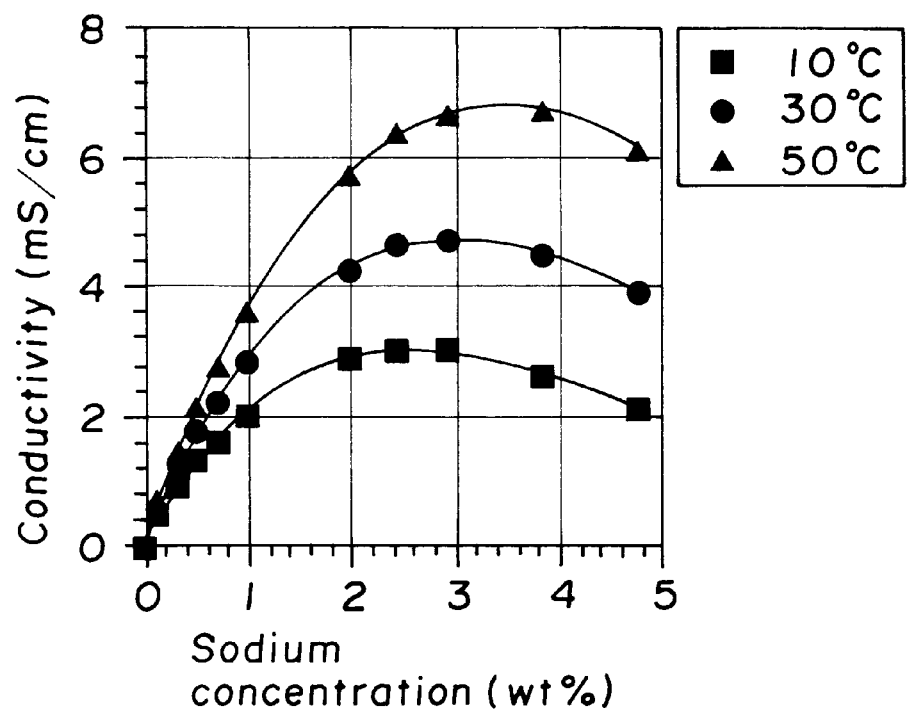
FIG. 1 shows the characteristic curves of conductivity showing the relationships between sodium concentration in alcohol and conductivity of alcohol at alcohol temperatures of 10, 30 and 50° C., respectively.
Figure 2:
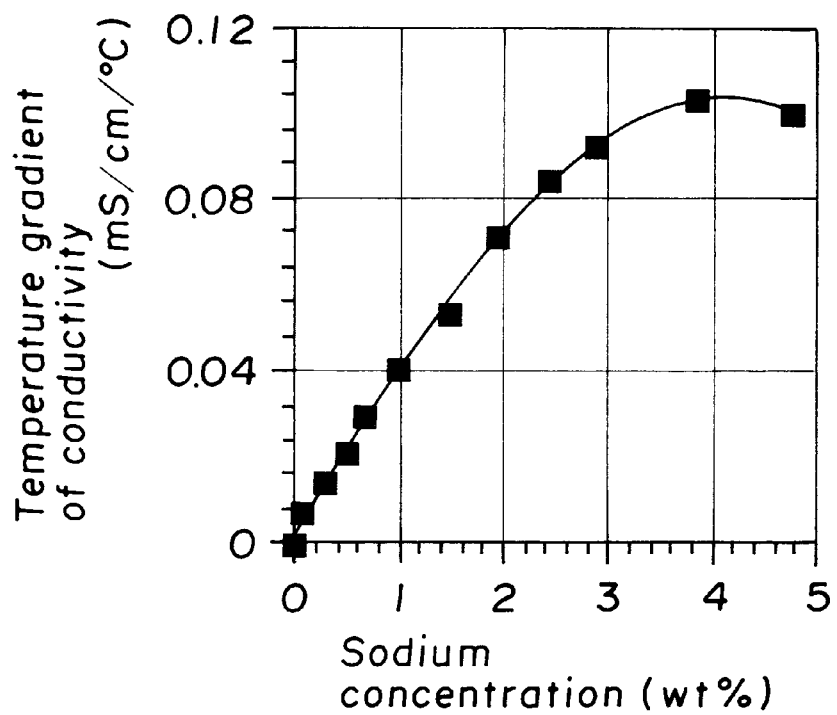
FIG. 2 shows a temperature correction curve showing the change in conductivity per unit degree centigrade of alcohol temperature (temperature gradient of conductivity) versus sodium concentration in alcohol.

The determination of sodium concentration in alcohol according to the present invention must be preceded by the preparation of the characteristic curve of conductivity as shown in FIG. 1 and a temperature correction curve as shown in FIG. 2. The characteristic curves of conductivity shown in FIG. 1 represent the relationships between sodium concentration in alcohol (wt %) and conductivity (mS/cm) as observed at alcohol temperatures of 10, 30 and 50° C. At each alcohol temperature, the conductivity increases linearly up to the sodium concentration of about 1 to 2 wt %, and then tends to lower with an increase in the sodium concentration. More precisely, the conductivity values at 10, 30 and 50° C. peak at sodium concentrations of about 2.5, 3.5 and 4.0 wt %, respectively, and tend to lower at sodium concentrations higher than these values. It may be presumed that a compound formed from sodium and alcohol is causative of lowering the conductivity at a sodium concentration higher than a certain level.

The temperature correction curve shown in FIG. 2 is a graph showing the relationship between sodium concentration in alcohol (wt %) and change in conductivity per unit degree centigrade of alcohol temperature (temperature gradient, mS/cm/° C.).

After the standard curves as shown in FIGS. 1 and 2 have been prepared, the determination of sodium concentration in an actual sample alcohol is conducted by examining the sample alcohol for conductivity and temperature, subjecting the measured conductivity to temperature correction according to the temperature correction curve shown in FIG. 2, and determining the correct sodium concentration in the sample alcohol on the basis of the corrected conductivity thus obtained.

EXAMPLES

There are two methods for calculating sodium concentration in alcohol from the measured conductivity and temperature of alcohol through temperature correction. The methods will now be described in the following Examples.

Example 1

[The case where the sodium concentration in the sample alcohol is approximately known.]

A case will now be inspected, in which the measured temperature and conductivity of the sample alcohol are as follows:

Measured temperature: 20° C.

Measured conductivity: 2.2 mS/cm (a) The temperature gradient of conductivity in this case is determined according to the correction curve shown in FIG. 2.

When the sodium concentration determined in the precedent measuring run is 1 wt %, the temperature gradient of conductivity is 0.04 mS/cm/° C. as read from the correction curve shown in FIG. 2.

(b) The measured conductivity is corrected by multiplying the difference between the alcohol temperature at measuring the conductivity and that at preparing the characteristic curve shown in FIG. 1 (i.e., 10, 30 or 50° C.) by the temperature gradient of conductivity and adding the thus obtained correction value to the measured conductivity or subtracting it therefrom.

The conductivity at 30° C. is calculated from the conductivity measured at 20° C. through correction according to the following formula:

corrected conductivity=(30° C.−20° C.)×0.04 mS/cm/° C.+2.2 mS/cm=2.6 mS/cm (c) The sodium concentration is determined on the basis of the corrected conductivity according to the characteristic curve of conductivity shown in FIG. 1.

The conductivity read on the characteristic curve at a sodium concentration of 1 wt % and an alcohol temperature of 30° C. is 2.4 mS/cm, while the corrected conductivity is 2.6 mS/cm. This fact means that the dissolution of sodium into alcohol still continues, in other words, the removal of sodium is not completed. If the removal has been completed, no increase must be found in the conductivity, i.e., the conductivity read on the characteristic curve must be equal to the corrected conductivity.

Example 2

[The case where the sodium concentration in the sample alcohol is unknown at all.]

(a) The conductivity of the sample alcohol is measured at two temperatures different from each other.

A case will now be inspected, in which the measured conductivity values and temperatures are as follows:

Measurement 1 measured temperature: 15° C. measured conductivity: 1.0 mS/cm

Measurement 2 measured temperature: 25° C. measured conductivity: 1.4 mS/cm (b) The temperature gradient of conductivity is calculated form the measured temperatures and measured conductivity values of the sample alcohol.

The temperature gradient of conductivity (the increase in conductivity per unit degree centigrade) can be calculated by the following formula:

(1.4 mS/cm−1.0 mS/cm)/(25° C.−15° C.)=0.04 mS/cm/° C.

(c) The sodium concentration is determined according to the temperature correction curve shown in FIG. 2.

The sodium concentration corresponding to the temperature gradient of 0.04 mS/cm/° C. is found to be 1 wt % as read on the correction curve.

When the conductivity of a sample alcohol is measured at a temperature equal to that employed in preparing the characteristic curve shown in FIG. 1, i.e., at 10, 30 or 50° C., the sodium concentration in the sample alcohol can also be read directly from FIG. 1 on the basis of the conductivity thus measured.

As will be understood from the above description, sodium concentration in alcohol can be determined accurately and speedily by measuring the conductivity and temperature of alcohol and subjecting the measured conductivity to temperature correction.

Further, the on-line monitoring of sodium concentration in alcohol can effectively be conducted by processing the electrical signals sent from a conductivity detector and a temperature detector.

The method of the present invention enables continuous monitoring of sodium concentration in alcohol, automation of the operation, and remarkable reduction of the operators so as to permit speedy and accurate grasp of progress of sodium removal by alcohol, thus improving the safeness of the removal. Further, the timing of discontinuing the removal and a suitable timing of exchanging an alcoholic washing fluid can be judged exactly, which reduces the amount of alcohol used or that of waste alcohol and lowers the cost.

What is claimed is:

1. A method for determining sodium concentration in alcohol, which comprises preparing a characteristic curve of conductivity showing the relationship between sodium concentration in alcohol and conductivity of alcohol as observed at a predetermined temperature and a temperature correction curve showing the change in conductivity per unit degree centigrade of alcohol temperature versus sodium concentration in alcohol, measuring the conductivity and temperature of a sample alcohol simultaneously, subjecting the measured conductivity to temperature correction according to the temperature correction curve, and determining the sodium concentration in the sample alcohol on the basis of the corrected conductivity thus obtained.

* * * * *